US008445873B2

(12) United States Patent
Banine et al.

(10) Patent No.: US 8,445,873 B2
(45) Date of Patent: May 21, 2013

(54) SYSTEM AND METHOD FOR DETECTING AT LEAST ONE CONTAMINATION SPECIES IN A LITHOGRAPHIC APPARATUS

(75) Inventors: Vadim Yevgenyevich Banine, Helmond (NL); Levinus Pieter Bakker, Helmond (NL); Ralph Kurt, Eindhoven (NL); Johannes Hubertus Josephina Moors, Helmond (NL); Lucas Henricus Johannes Stevens, Eindhoven (NL); Peter Cornelis Zalm, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 13/478,446

(22) Filed: May 23, 2012

(65) Prior Publication Data

US 2012/0241610 A1 Sep. 27, 2012

Related U.S. Application Data

(62) Division of application No. 13/021,226, filed on Feb. 4, 2011, now Pat. No. 8,217,347, which is a division of application No. 11/311,623, filed on Dec. 20, 2005, now Pat. No. 7,897,110.

(51) Int. Cl.
*G21G 5/00* (2006.01)

(52) U.S. Cl.
USPC .......... 250/492.24; 422/186.21; 422/83; 250/311; 250/307; 250/251; 355/67; 355/53

(58) Field of Classification Search
USPC ....... 250/491.1, 492.24, 311, 492.2; 356/215, 356/401, 53; 422/83
See application file for complete search history.

(56) References Cited

U.S. PATENT DOCUMENTS

| | | | |
|---|---|---|---|
| 5,641,423 A | 6/1997 | Bridges et al. | |
| 6,409,837 B1 | 6/2002 | Hillman | |
| 6,694,284 B1 * | 2/2004 | Nikoonahad et al. | 702/155 |
| 6,934,017 B2 * | 8/2005 | Kircher | 356/215 |
| 7,034,474 B2 * | 4/2006 | Yang et al. | 318/135 |
| 7,138,629 B2 * | 11/2006 | Noji et al. | 250/311 |
| 7,897,110 B2 | 3/2011 | Banine et al. | |
| 8,217,347 B2 | 7/2012 | Banine et al. | |
| 2002/0083409 A1 | 6/2002 | Hamm | |
| 2003/0031589 A1 | 2/2003 | Martin et al. | |

(Continued)

FOREIGN PATENT DOCUMENTS

| | | |
|---|---|---|
| EP | 1 452 851 A1 | 9/2004 |
| GB | 2 360 583 A | 9/2001 |

OTHER PUBLICATIONS

Beysens, D., "The formation of dew," Atmosphere Research, vol. 39, Oct. 1995; pp. 215-237.

(Continued)

*Primary Examiner* — Sally Merkling
(74) *Attorney, Agent, or Firm* — Sterne, Kessler, Goldstein & Fox P.L.L.C.

(57) ABSTRACT

A system for detecting at least one contamination species in an interior space of a lithographic apparatus, including: at least one monitoring surface configured to be in contact with the interior space, a thermal controller configured to control the temperature of the monitoring surface to at least one detection temperature, and at least one detector configured to detect condensation of the at least one contamination species onto the monitoring surface.

20 Claims, 5 Drawing Sheets

U.S. PATENT DOCUMENTS

2004/0227102 A1* 11/2004 Kurt et al. .................. 250/491.1
2007/0140910 A1    6/2007 Banine et al.
2011/0121177 A1    5/2011 Banine et al.

OTHER PUBLICATIONS

Non-Final Rejection mailed Oct. 28, 2009, for U.S. Appl. No. 11/311,623, filed Dec. 20, 2005; 9 pages.
Final Rejection mailed Apr. 28, 2010, for U.S. Appl. No. 11/311,623, filed Dec. 20, 2005; 10 pages.
Notice of Allowance mailed Oct. 26, 2010 for U.S. Appl. No. 11/311,623, filed Dec. 20, 2005; 7 pages.
Non-Final Rejection mailed Apr. 13, 2011 for U.S. Appl. No. 13/021,226, filed Feb. 4, 2011; 13 pages.
Final Rejection mailed Sep. 23, 2011 for U.S Appl. No. 13/021,226, filed Feb. 4, 2011; 11 pages.
Notice of Allowace mailed Mar. 20, 2012 for U.S. Appl. No. 13/021,226, filed Feb. 4, 2011; 9 pages.

* cited by examiner

SYSTEM AND METHOD FOR DETECTING AT LEAST ONE CONTAMINATION SPECIES IN A LITHOGRAPHIC APPARATUS

CROSS REFERENCE TO RELATED APPLICATIONS

This application is a divisional of U.S. patent application Ser. No. 13/021,226, filed Feb. 4, 2011 now U.S. Pat. No. 8,217,347, which is a divisional of U.S. patent application Ser. No. 11/311,623, filed Dec. 20, 2005 (now U.S. Pat. No. 7,897,110, issued Mar. 1, 2011), and both are incorporated by reference herein in their entirety,

BACKGROUND OF THE INVENTION

1. Field of the Invention

The present invention relates to a system and method for detecting at least one contamination species in a lithographic apparatus.

2. Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of one, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In case of an interior space, for example a vacuum, it is generally desired to monitor the interior space for contamination. This is the case, for example, when the space is used in a lithographic process, or for instance when the space is included in a lithographic apparatus. In that case, it is desired to detect contamination quickly—preferably within a fraction of a second—so that a lithographic process can be halted immediately to prevent contamination sensitive optics being spoiled by the contamination. However, the interior space can also be applied in different fields, for instance general semiconductor industry, general vacuum technology industry, space technology and the-like. The present invention can therefore also explicitly be applied outside the field of lithography.

Various methods and devices are known from the prior art, which are configured for detecting contamination.

United States Patent Application Publication No. 2002/0083409 A1 relates to EUV lithography devices and processes, wherein a quartz crystal microwave is use as a measuring device.

European Patent Application Publication No. EP 1 452 851 A1 relates to a method and device for measuring contamination of a surface of a component of a lithographic apparatus. The measuring device has a radiation transmitter device for projection radiation on at least a part of the surface and a radiation receiver device for receiving radiation from the component.

BRIEF SUMMARY OF THE INVENTION

It is desirable to provide an improved system and method for monitoring contamination, wherein the occurrence of contamination can be detected swiftly, using a relatively simple, inexpensive monitoring device.

According to an aspect of the invention, there is provided a system for detecting at least one contamination species in an interior space, the system including: at least one monitoring surface configured to be in contact with the interior space; a thermal controller which is configured to control the temperature of the monitoring surface to at least one detection temperature; at least one detector which is configured to detect condensation of the at least one contamination species onto the monitoring surface; wherein the detection temperature is close to or lower than (i.e., less than or about) a saturation temperature of the at least one contamination species, to condense the at least one contamination species onto the monitoring surface when the pressure of that contamination species exceeds a given threshold pressure.

According to an aspect of the invention, there is provided a system for detecting at least one species in a space, the system including: at least one monitoring surface configured to be in contact with the space; a thermal controller which is configured to control the temperature of the monitoring surface to at least one detection temperature; at least one detector which is configured to detect condensation of the at least one species onto the monitoring surface; the detection temperature being close to or lower than (i.e., less than or about) a saturation temperature of the at least one species to condense the at least one species onto the monitoring surface, when the pressure of that species exceeds a given threshold pressure; wherein the monitoring surface is a surface of the detector.

According to an aspect of the invention, there is provided a lithographic apparatus arranged to transfer a pattern from a patterning device onto a substrate.

According to an aspect of the invention, there is provided a lithographic apparatus comprising: an illumination system configured to condition a radiation beam; a support constructed to support a patterning device, the patterning device being capable of imparting the radiation beam with a pattern in its cross-section to form a patterned radiation beam; a substrate table constructed to hold a substrate; and a projection system configured to project the patterned radiation beam onto a target portion of the substrate.

The lithographic apparatus can comprise at least one monitoring system according to the invention.

Also, an aspect of the invention provides a vacuum system, comprising at least one system for monitoring contamination.

In an aspect of the invention, a method for monitoring contamination in an interior space comprises: providing at least one monitoring surface which contacts the interior space; controlling the temperature of the monitoring surface to at least one detection temperature, which detection temperature is close to or lower than (i.e., less than or about) a saturation temperature of at least one contamination species to condense the at least one contamination species onto the monitoring surface, when the pressure of that contamination species exceeds a given threshold pressure; and monitoring to detect whether the at least one contamination species condenses onto the monitoring surface.

In a method according to the invention for monitoring at least a first and a second contamination species in an interior space, the saturation temperature of the first contamination species can be higher than the saturation temperature of the second contamination species at given threshold pressures. The method according to the invention can comprise: providing at least one monitoring surface which contacts the interior space; controlling the temperature of the monitoring surface to at least a first detection temperature, which detection temperature is close to or lower than (i.e., less than or about) the saturation temperature of the first contamination species, but higher than the saturation temperature of the second contamination species; controlling the temperature of the monitoring surface to at least a second detection temperature, which second detection temperature is close to or lower than (i.e., less than or about) the saturation temperature of the second contamination species; and monitoring to detect whether the at least first and second contamination species condense onto the monitoring surface.

Further, the invention provides a system for detecting at least one contamination species in an interior space, including: at least one monitoring surface configured to be in contact with the interior space; a thermal controller which is configured to control the temperature of the monitoring surface to at least one detection temperature; at least one detector which is configured to detect condensation of the at least one contamination species onto the monitoring surface; wherein the at least one detection temperature is lower than 295° K.

Also, in an aspect, a method for monitoring contamination in an interior space, comprises: providing at least one monitoring surface which contacts the interior space; controlling the temperature of the monitoring surface to at least one detection temperature, wherein the at least one detection temperature is lower than 295° K.; and monitoring for condensation of the at least one contamination species onto the monitoring surface.

An aspect of the invention provides a lithographic device manufacturing method, which can comprise a monitoring method for monitoring contamination.

According to an aspect of the invention, there is provided a use of a quartz crystal microwave detector or a surface acoustic wave detector at subsequently different detection temperatures, for monitoring respective different species of contamination in an interior space.

According to an aspect of the invention, there is provided a device manufacturing method comprising projecting a patterned beam of radiation onto a substrate.

According to an aspect of the invention, there is provided a device manufactured by a lithographic manufacturing method.

An aspect of the invention provides a computer program or computer program product, comprising program code portions for performing steps of a contamination monitoring method.

In an aspect of the invention, there is provided a system for detecting at least one contamination species in a vacuum, the system comprising: at least one cathode having a surface configured to emit electrons into said vacuum; at least one detector configured to detect electrons that are emitted by said cathode; wherein the cathode is configured to emit a first current of electrons when the cathode surface is substantially not contaminated by said species, and to emit a second current of electrons when the cathode surface is contaminated by said species.

The invention also provides an array of systems for monitoring contamination. The invention also provides a vacuum system, comprising at least one contamination monitoring system.

An aspect of the invention is provided by a lithographic apparatus, comprising at least one contamination monitoring system.

According to the invention, a method for monitoring at least one contamination species in a vacuum can comprise: providing at least one cathode, which cathode is configured to emit a first current of electrons when the cathode surface is substantially not contaminated by the contamination species, and to emit a second current of electrons when the cathode surface is contaminated by the contamination species; heating the cathode; and providing a detector for detecting electrons that are emitted by said heated cathode.

Also, an aspect of the invention provides a lithographic device manufacturing method, including a contamination monitoring method.

An aspect of the invention provides the use of a cathode containing $LaB_6$ or $CeB_6$ for monitoring contamination.

Another aspect of the invention provides the use of at least one carbon nanotube for monitoring contamination.

Also, an aspect of the invention provides a contamination monitor, at least consisting of $LaB_6$ (full name: Lanthanum Hexaboride) or $CeB_6$ (full name: Cesium Hexaboride).

The invention also provides a cathode surface, at least containing $LaB_6$ or $CeB_6$.

In an aspect of the invention, there is provided a system for detecting at least one contamination species in a first vacuum, the system comprising: at least one cathode having a surface configured to emit electrons into a second vacuum; a fluid connection between the first vacuum and the second vacuum; at least one detector configured to detect electrons that are emitted by said cathode; wherein the cathode is configured to emit a first current of electrons when the cathode surface is substantially not contaminated by said at least one contamination species, and to emit a second current of electrons when the cathode surface is contaminated by said at least one contamination species.

Also, in an aspect of the invention, a system for detecting at least one contamination species in a vacuum, includes: at least one field emitter having at least one tip configured to emit electrons into said vacuum; at least one detector configured to detect electrons that are emitted by said field emitter; wherein the field emitter is configured to emit a first current of electrons when the field emitter tip is substantially not contaminated by said at least one contamination species, and to emit a second current of electrons when the field emitter tip is contaminated by said at least one contamination species.

A method for monitoring at least one contamination species in a vacuum can include: providing at least one field emitter, which field emitter is configured to emit a first current of electrons when a tip of the field emitter is substantially not contaminated by the at least one contamination species, and to emit a second current of electrons when the tip is contaminated by the at least one contamination species; and providing a detector for detecting electrons that are emitted by said field emitter.

Besides, in an aspect of the invention, a field emitter tip can contain at least $LaB_6$ or $CeB_6$.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF THE INVENTION

Figure 1:
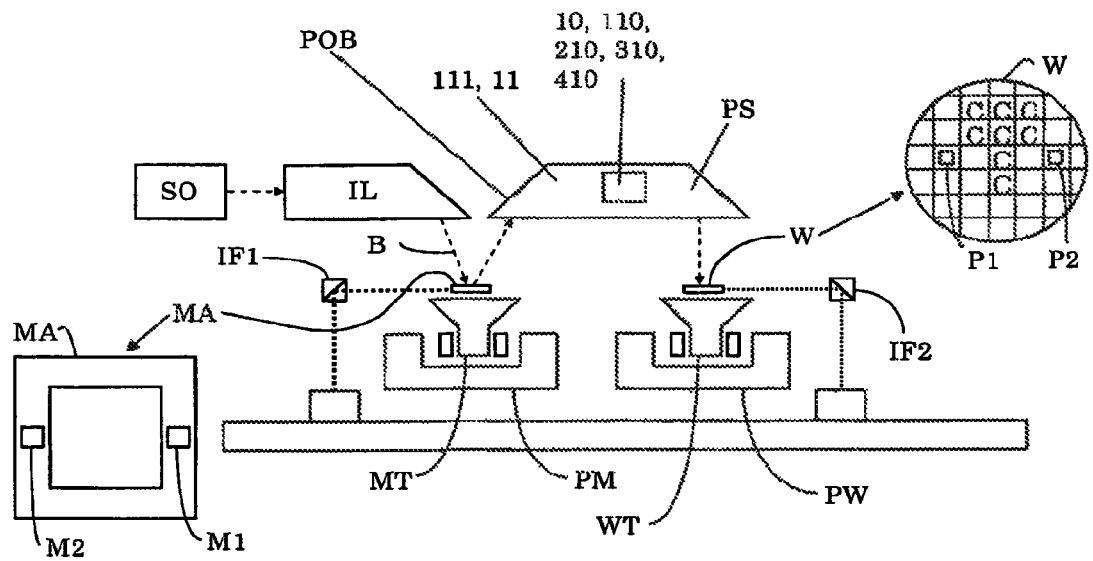
FIG. 1 depicts a lithographic apparatus according to an embodiment of the invention.

FIG. 1 schematically depicts a lithographic apparatus according to one embodiment of the invention. The apparatus comprises: an illumination system (illuminator) IL configured to condition a radiation beam B (e.g., UV radiation or other radiation); a support structure (e.g., a mask table) MT constructed to support a patterning device (e.g., a mask) MA and connected to a first positioner PM configured to accurately position the patterning device in accordance with certain parameters; a substrate table (e.g., a wafer table) WT constructed to hold a substrate (e.g., a resist-coated wafer) W and connected to a second positioner PW configured to accurately position the substrate in accordance with certain parameters; and a projection system (e.g., a refractive projection lens system) PS configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e., bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system."

As here depicted, the apparatus is of a reflective type (e.g., employing a reflective mask). Alternatively, the apparatus may be of a transmissive type (e.g., employing a transmissive mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system comprising, for example, suitable directing mirrors and/or a beam expander. In other cases the source may be an integral part of the lithographic apparatus, for example when the source is a mercury lamp. The source SO and the illuminator IL, together with the beam delivery system, if required, may be referred to as a radiation system.

The illuminator IL may comprise an adjuster for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator and a condenser. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PS, which focuses the beam onto a target portion C of the substrate W. With the aid of the second positioner PW and position sensor IF2 (e.g., an interferometric device, linear encoder or capacitive sensor), the substrate table WT can be moved accurately, e.g., so as to position different target portions C in the path of the radiation beam B. Similarly, the first positioner PM and another position sensor IF 1 can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e., a single dynamic exposure). The velocity and direction of the substrate table WT relative to the mask table MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
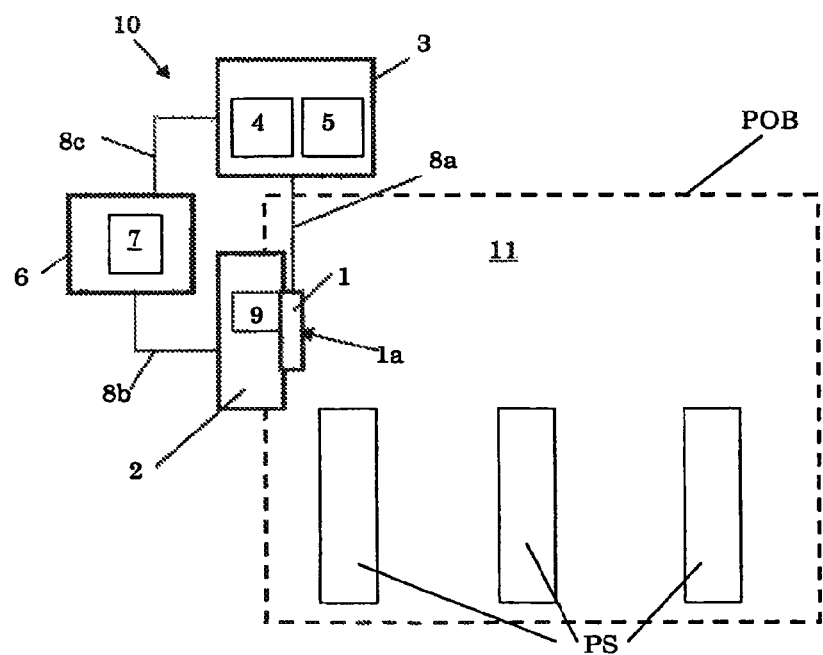
FIG. 2 depicts an embodiment of a contamination monitoring system.
Figure 4:
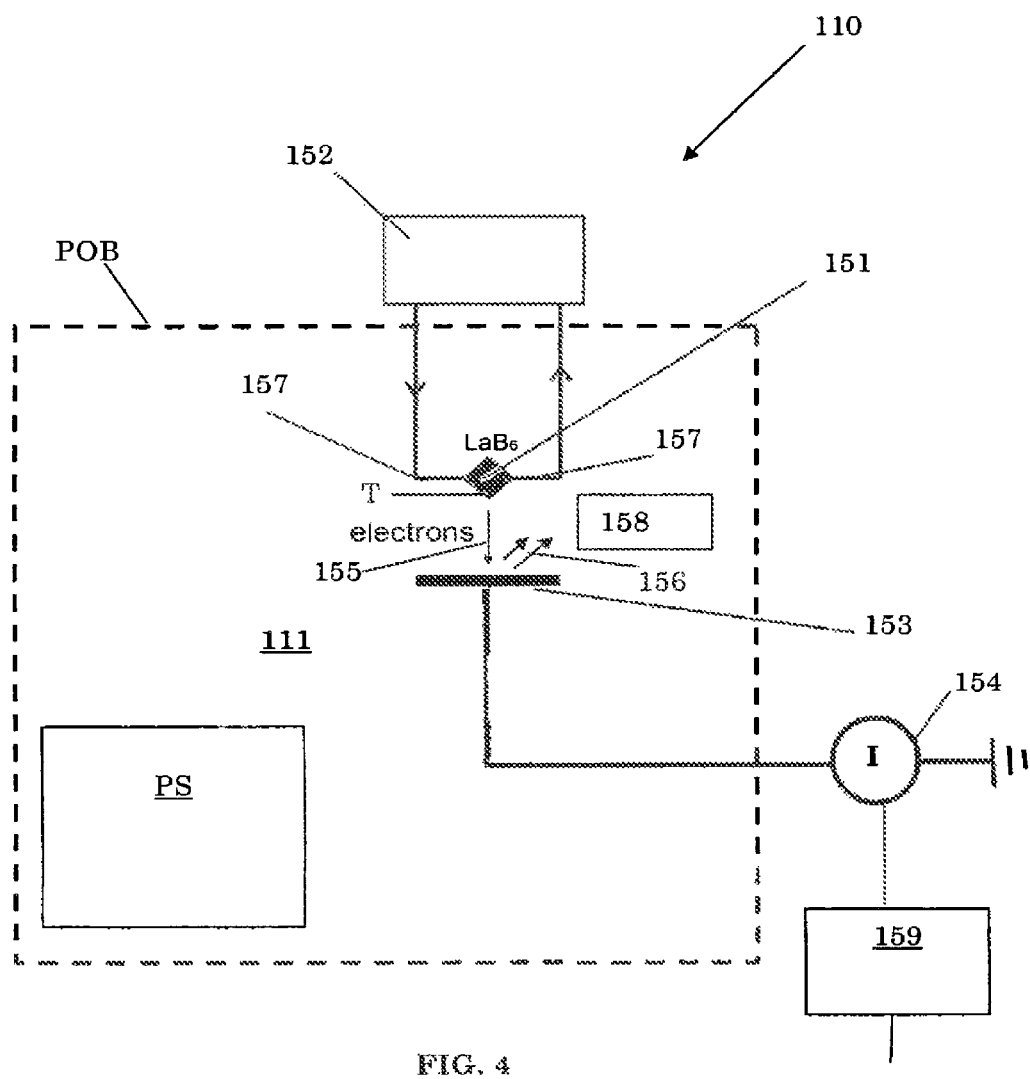
FIG. 4 depicts a second embodiment of a contamination monitoring system.

The lithographic apparatus can include a system 10, 110, 210, 310 for detecting at least one contamination species in a vacuum interior space 11, 111 of the apparatus. The monitoring system 10, 110, 210, 310 can be located in various locations of the device, for example in or near the projection system PS, in the projection optics box POB, in a reticle zone, in a substrate zone or in other locations of the apparatus. FIGS. 2 and 4 show examples, wherein the interior space 11, 111 is a space in the projection optics box POB, containing at least part of a projection system PS.

The interior vacuum space 11, 111 can be located, for example in a vacuum chamber. The vacuum of the vacuum space 11, 111 can have varying vacuum pressures, which can depend, for example, on the radiation type of the radiation beam B used in the lithographic apparatus. Also, an interior space that has been provided with at least one monitoring device 10, 110, 210, 310, 410 can be, for example, a space which also contains the patterning means, a space which also contains the substrate support, or another space of the apparatus.

In an embodiment of the invention, the contamination monitoring system 10 can include: at least one monitoring surface 1a which is in contact with the interior space 11 during use; a thermal controller 2 which is configured to control the temperature of the monitoring surface 1a to at least one detection temperature; at least one detector 1 which is configured to detect condensation of the at least one contamination species onto the monitoring surface 1a.

An embodiment of such a system is depicted schematically in FIG. 2. This embodiment includes only one monitoring surface and only one detector. Alternatively, a plurality of detectors and/or a plurality of monitoring surfaces is being provided, for example, to monitor at different locations in the apparatus and/or to monitor different contamination species. When the detectors or monitoring surfaces are at different temperatures, the difference between the two respective monitoring signals can be due to a contaminant species condensing or significantly absorbing at the lower temperature of the two monitors.

In the embodiment of FIG. 2, the monitoring surface 1a is a surface of the detector 1. For example, the detector 1 can be a quartz crystal monitor detector (QCM) or a surface acoustic wave detector (SAW). Such detectors are known to the person skilled in the art. The detector 1 can be configured to provide a detector signal which at least depends on the amount of contamination which has been condensed on the monitoring surface, for example, in case the detector is a QCM detector or a SAW detector. QCM and SAW detectors are very sensitive to materials that are received by their monitoring surfaces. For example, a QCM or SAW detector can even detect the growth of less than a single monolayer of many different materials onto the respective monitoring surface. Besides, such a detector is relatively inexpensive. Also, for example, light can be used to detect adsorption of contamination, for example infrared light.

Besides, a top surface, for example a detection surface 1a, of the detector can include the same material as the material of parts of the projection system that are in contact with the interior space 11. For example, these parts can be optical elements that extend in or are in contact with the interior space, for example, lens elements, mirror elements and/or other elements of the projection system PS.

Also, the detection surface 1a can be provided with a certain surface roughness to improve its sensitivity for adsorption of contamination.

The thermal controller 2 can be configured to control the temperature of the monitoring surface 1a to least two different detection temperatures. For example, the thermal controller 2 can be configured to provide a temperature sweep of the temperature of the monitoring surface 1a.

In an aspect of the invention, the thermal controller 2 can be configured to control the temperature of the monitoring surface to a plurality of temperatures in the range between about 77K-400° K. For example, the thermal controller 2 can be configured to control the temperature of the monitoring surface to a plurality of temperatures in the range between about 77K-293° K.

Besides, the monitoring surface 1a can be kept at a relatively low temperature to accumulate contaminant for a long time. After this, the temperature can be slowly increased (e.g., linearly) and the mass decrease can be measured. In this way (i.e through temperature programmed desorption), the kind of contaminant can be deduced in a simple manner.

The thermal controller 2 can be configured in various ways. As an example only, the thermal controller 2 can include at least one element that is thermally conditioned by a fluid. The thermal controller can include at least one cryogenically cooled element, and/or at least one Peltier element. The thermal controller can include at least one heater. For example, the thermal controller can include one or more electrical heaters, electromagnetic heaters, induction heaters and/or different heaters. Also, the thermal controller can comprise one or more temperature sensors, configured to measure the temperature of the thermal controller, to measure the temperature of the detector 1, and/or to measure the temperature of the monitoring surface 1a. Such a temperature sensor can be configured in various ways, and may include for example one or more thermocouples, or other temperature sensors. One such temperature sensor has been schematically shown in FIG. 2 at reference sign 9.

In the embodiment of FIG. 2, the thermal controller 2 is in thermal contact with the detector 1. For example, a back-side of the detector 1, which is faced away from said monitoring surface 1a, can be attached to the thermal controller 1. Alternatively, the thermal controller 2 and the monitoring surface 1a of detector 1 can be thermally connected in another way, to control the temperature of the monitoring surface 1a.

Also, the thermal controller 2 can comprise a control device, for example, an electronic device, a programmable device, a computer and/or another suitable device. An example of such a control device is schematically indicated in FIG. 2 at reference sign 6. The control device 6 of the thermal controller 2 can be configured to have the thermal controller 2 perform the above-mentioned functions, for example, to control the thermal controller 2 to modify and/or maintain the temperature of the monitoring surface 1a to and/or at a desired detection temperature.

The control device 6 can be configured to use sensor information of the temperature sensor 9 as feed-back for controlling the temperature of the monitoring surface 1a. Further, a computer program or computer program product can be provided, comprising program code portions which are configured to have the thermal controller 2 modify and/or maintain the temperature of the monitoring surface 1a to and/or at a desired temperature, when run by the control device 6.

In FIG. 2, the control device 6 of the thermal controller 2 is shown spaced-apart from the thermal controller 2 and the thermal sensor 9, and a communication line 8b is included to provide communication between these parts 6, 2, 9. Alternatively, the control device 6 of the thermal controller 2 and the thermal controller 2 can be joined together in a single device.

The contamination monitoring system 10 can also include a processor for processing the detector signal. The processor can be configured in various ways. The processor can be configured to determine the amount of contamination which is condensed on the monitoring surface 1a, using the detector signal, at a given temperature of that surface. The processor can also be configured to process the detector signal to detect condensation of at least one species of contamination onto the monitoring surface 1a. Also, the processor can be configured to generate an alarm signal in case the determined amount of the at least one species of contamination exceeds a certain threshold amount, or in case a certain adsorption of the at least one species of contamination is detected. For example, the processor can be configured to generate an alarm signal in case substantially at least one monolayer of the contamination species has been condensed onto the monitoring surface 1a. In an aspect of the invention, the processor comprises a memory for storing the threshold amount of at least one contamination species.

An embodiment of such a processor is schematically indicated in FIG. 2 at reference sign 3. For example, the processor can include a memory 5, which the processor can use to store temperature calibration data of the monitor device, and/or to store said threshold amount of at least one contamination species. Also, the processor 3 can include one or more calculating devices 4 to perform calculations and/or comparisons, for example to derive the amount of at least one species of contamination which is condensed on the monitoring surface 1a, to generate an alarm signal in case the determined amount of the at least one species of contamination exceeds a certain threshold amount, and/or to perform other functions. Further, a computer program or computer program product can be provided, comprising program code portions for performing at least such calculations and/or comparisons when run by the processor.

In FIG. 2, the processor is shown spaced-apart from the detector 1 and the thermal controller 2. In the depicted embodiment, the processor 3 is linked to the detector 1 and the control device 6 of the thermal controller 2 by suitable communication lines 8a, 8c respectively. Alternatively, the processor and the detector can be joined together in a single device. Also, alternatively, the processor and the control device 6 of the thermal controller 2, or the thermal controller 2 as such, can be joined together in a single device.

In an aspect of the invention, the detection temperature is close to or lower than (i.e., less than or about) the saturation temperature of the at least one contamination species to be detected in the interior space during use, at a given pressure. The detection temperature can be close to or lower than a saturation temperature of the at least one contamination species to condense the at least one contamination species onto the monitoring surface, when the pressure of that contamination species exceeds a given threshold pressure. For example, the threshold pressure can be about $10^{-3}$ mbar or less. Also, different threshold pressures can be used. The threshold pressure depends, for example, on the maximum amount of a respective contamination species that can be allowed into the interior space 11, before the contamination species can harm components of the lithographic apparatus, and/or hamper a lithographic process, for the case that the monitoring system is used in lithography.

The saturation temperature is the temperature at which contamination vapour at a given pressure will begin to condense. The saturation temperature is also known as dew point temperature. If the temperature of the monitoring surface 1a is above the saturation temperature, the degree of the surface filling (number of molecules on the surface/max number of places for these molecules in a monolayer) on a monitoring surface 1a will be below 1. Under such conditions, the adsorption-desorption equilibrium will be such that the surface filling is low. If the temperature reaches the saturation temperature, a fast growth of contamination at the surface 1a of the detector 1 can occur due to the condensation (such as during fog forming of water). As a result of the fast condensation, the degree of the surface filling on the monitoring surface 1a becomes substantially 1, and one or more monolayers of said contamination species can be formed swiftly on the monitoring surface 1a.

For example, the detection temperature can be about equal to the saturation temperature of the contamination species to be detected, or a bit lower, for example, not more than about 10K below said saturation temperature. To the skilled person, it will be clear that the saturation temperature of a contamination species depends on the pressure of that species in the interior space 11. Saturation temperatures of many contamination species at certain pressures can be found in literature. Besides, it will be clear to the skilled person that he can find a saturation temperature of a certain contamination species, at a certain pressure, by experiment.

Another way is to operate the monitoring system is to maintain the monitoring surface at a temperature that is lower than a surface temperature of the optics (which can be, for example, about 22° C. or 295° K.). At this temperature, the surface filling on the monitoring surface can be larger than the optics, which can than be detected. For example, the temperature of the monitoring surface can be lower than 275° K.

The control device 6 of the thermal controller 2 can comprise a memory to store a predetermined threshold pressure or predetermined threshold pressure related data of each contamination species, wherein the thermal controller 2 is configured to determine each respective saturation temperature from the threshold pressure or threshold pressure related data of each contamination species. Such a determination can be achieved, for example, using suitable calculations and/or data lists. The threshold related data can include, for example, a maximum density, a maximum mass, a maximum weight % and/or a maximum volume % that a contamination species may reach in the interior space 11, or a certain surface occupation on the monitoring surface. Alternatively, the control device 6 of the thermal controller 2 can comprise a memory to directly store a predetermined detection temperature and/or saturation temperature of each contamination species, which is to be monitored. Such a memory is shown schematically at reference sign 7.

The at least one species of contamination can be selected for example from the group consisting of: water vapour; hydrocarbon vapours; and volatile gasses, for example $CO_2$, $O_2$, $O_3$, and/or other volatile gasses.

The detection temperature can be lower than the detection temperature of parts of the projection system PS, for example parts that extend in the interior space, which can be lens elements, mirror elements and/or other elements of the projection system PS. The detection temperature can be, for example, lower than about 295.degree. K. For example, in case the contamination species is water vapour and the respective threshold pressure is about 1 mbar, the detection temperature can be lower than 200.degree. K., for example if the pressure in the interior space 11 is a vacuum pressure.

Figure 3:
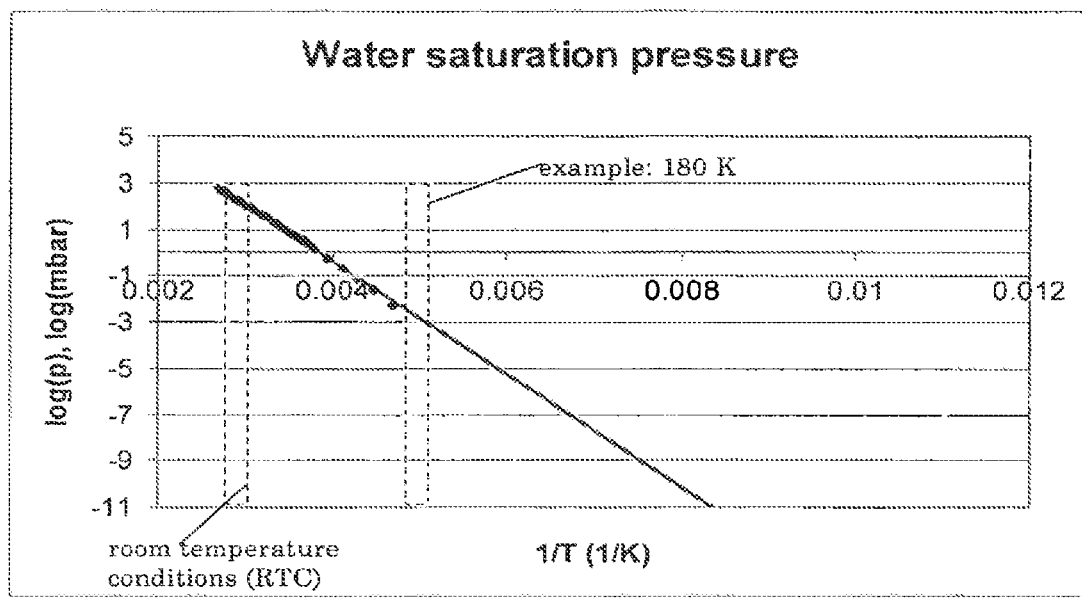
FIG. 3 depicts a graph of water saturation pressure versus temperature.

FIG. 3 shows a graph of water saturation pressure versus temperature. Similar graphs can be drawn for other contamination species.

The saturation temperature of water, at a given pressure, can be derived from FIG. 3. For example, a water saturation pressure of about 1 mbar is reached at a respective saturation temperature of about 250° K. ($T^{-1}$=0.004). At room temperature conditions RTC, the water saturation pressure is about 20 mbar. A saturation pressure of about $10^{-3}$ mbar will be reached at a saturation temperature will be about 180° K. Thus, at 180° K., water will start condensing much earlier onto the monitoring surface 1a of the detector 1, at much lower partial pressures, than at room temperature.

In an aspect of the invention, the condensation detector 1 is being thermally calibrated, or corrected for thermal offset, in a contamination free environment first, before the detector 1 is being used for the monitoring of contamination. Detector calibration can be carried out, for example, in the interior space 11, or in a different location. The thermal calibration can take into account, for example, temperature dependent detector drift. Detector drift can depend on the detector temperature as such, and/or the speed and/or type of variation of the detector temperature, for example, detector drift due to the sweeping of the monitoring surface 1a between different temperatures. Resulting calibration data can be stored, for example, in the processor 3, to be used during the monitoring of contamination, for example as offset data.

During use, the contamination monitoring system 10 can monitor for the presence of gaseous contamination in the interior space 11. During use, each contamination species can be assigned an individual threshold partial gas pressure, which can be a maximum allowable pressure for that species. Alternatively, each contamination species can be assigned individual threshold pressure related data, as has been mentioned above. Then, for example, a respective saturation temperature can be determined from the threshold pressure, or from threshold pressure related data, for each contamination species. Alternatively, the saturation temperature of a contamination species, at which temperature a given maximum amount of contamination species reaches the saturation pressure in the interior space 11, can already be predetermined.

The temperature of the monitoring surface 1a of the detector 1 can be controlled to at least one detection temperature during use. The detection temperature is close to or lower than the saturation temperature of the at least one contamination species to condense the at least one contamination species onto the monitoring surface 1a, when the pressure of that contamination species exceeds its threshold pressure.

The detector 1 monitors for condensation of the at least one contamination species onto the monitoring surface 1a.

For example, during use, the at least one detection temperature can be lower than 200° K., depending on the pressure in the interior space 11 and the contamination species to be monitored for. During use, each detection temperature can lie near or just below the saturation temperature of a respective contamination species to be detected, at a desired internal pressure of the interior space. For example, said detection temperature can lie not more than about 10° K. below said saturation temperature.

When only a small amount of a certain gaseous contamination species is present in the interior space 11, such that the pressure of the contamination species is below its preassigned threshold pressure, the contamination species will substantially not condense onto the monitoring surface 1a. This is due to the monitoring surface 1a having a detection temperature as mentioned above, which detection temperature is for example near the saturation temperature of that contamination species at the given threshold pressure.

When the amount of the gaseous contamination species in the space 11 rises, the pressure of the contamination species can reach its preassigned threshold pressure. In that case, the contamination species will condense onto the monitoring surface 1a. For example, the condensation of the contamination species leads to the growth of one or more monolayers of that species onto the monitoring surface 1a. This condensation can be detected by the detector 1. The detection of the condensation can also be transmitted by the detector 1 to the processor 3 using a monitoring (or detector) signal. This monitoring signal can at least depend on the amount of contamination which is condensed on the monitoring surface 1a.

For example, depending on the detector signal, the processor 3 can determine whether said threshold pressure has been reached, or whether the amount of contamination condensed on the monitoring surface, exceeds a certain threshold amount. Then, the processor 3 can generate an alarm signal and/or halt a lithographic process, for example in case the pressure of the contamination species rises above its threshold pressure.

EXAMPLE

Referring to FIG. 3 as example, in case of the contamination species being water, a threshold pressure can be set in the range of about $10^{-4}$-$10^{-3}$ mbar. Then, the respective detection temperature is about 180° K., which leads to a water saturation pressure near/at the monitoring surface 1 $a$ of just under $10^{-4}$-$10^{-3}$ mbar. If the gas pressure of the water in the interior space 11 stays below the saturation pressure, the degree of the surface filling (number of molecules on the surface/max number of places for these molecules in a monolayer) on the monitoring surface 1$a$ will be below 1. This means that the adsorption-desorption equilibrium will be such that the surface filling will be low. If the gas pressure in the volume, in this example water, reaches the saturated water pressure (or threshold pressure), a fast growth at the surface 1$a$ of the detector 1 will occur (such as during fog forming).

As an example, the characteristic time t of a layer formation depends on the velocity of molecules (v), their concentration n, and amount of places available at the surface (ns): $t=1/4*ns/(n*v)$.

Under conditions as described above (at a threshold pressure in the range of $10^{-4}$-$10^{-3}$ mbar, and a monitoring surface temperature of about 180° K.), it will take about 0.1-0.01 s to grow one layer onto the monitoring surface 1$a$. Such a layer can already be monitored. Therefore, alarm can be generated swiftly, so that degradation of apparatus parts by water contamination can be prevented.

In an aspect of the invention, during use, the temperature of the monitoring surface 1$a$ is subsequently being altered between at least two different detection temperatures, to monitor for at least two different contamination species having different condensation temperatures at the pressure of the interior space 11. Alternatively, at least two different monitoring surfaces can be used. In that case, the monitoring surfaces can be thermally conditioned to the different detection temperatures, so that each monitoring surface serves to monitor one of the different contamination species.

Also, the detection temperature can be being swept in a continuous or discrete manner, in a temperature range between a minimum and a maximum detection temperature. Herein, for instance, a sweep period can include about one or several seconds, or one or several minutes, or a different amount of time. In this way, different species, which have different condensation temperatures lying in that temperature range, can be monitored for. For example, when the saturation temperature of a first contamination species is higher than the saturation temperature of a second contamination species, at given threshold pressures, a monitoring method can include: controlling the temperature of the monitoring surface 1$a$ to at least a first detection temperature, which detection temperature is close to or lower than the saturation temperature of the first contamination species, but higher than the saturation temperature of the second contamination species; controlling the temperature of the monitoring surface 1$a$ to at least a second detection temperature, which second detection temperature is close to or lower than the saturation temperature of the second contamination species; and monitoring for condensation of the at least one contamination species onto the monitoring surface.

Besides, temperature programmed desorption of the monitor, for example, corrected for temperature dependent offset, can be utilized. As an example only, in that case, one of the contamination species can be hydrocarbon contamination, whereas the other contamination species can be water.

More generally, and as an example, during use, the detection temperature of the monitoring surface can be in the range between about 77° K.-400°. Also, the detection temperature of the monitoring surface can be in the range between about 77° K.-295° K. Also, different detection temperatures and detection temperature ranges can be applied, depending on the contamination which is to be monitored and the pressure in the interior space 11. By lowering the temperature of the monitoring surface 1$a$, contamination condensate will form more quickly thereon, at lower pressures—and therefore lower concentration—of that contamination.

For example, while exposing mirrors with EUV in EUV lithography systems, mirror damage can and will occur, if a leakage into EUV chamber of water or other contamination species happens. Damaging pressure levels of the leakage might be, for example, of the order of $10^4$-$10^{-3}$ mbar. When such a leakage occurs, a lithography exposure has to be stopped immediately (within 1 second).

For example, the monitoring surface can be set at low temperatures, e.g., temperatures just above liquid Nitrogen temperature, in order to obtain a substantial growth at the monitoring surface. The monitoring surface can be set either at the surface of an existing cryo panel pump in an EUV vacuum system, at a specifically made surface that is thermally conditioned with either a Peltier element, liquid nitrogen, or in another way. When the monitored growth of contamination on the monitoring surface undergoes a jump, it can mean that there is a sudden increase of the pressure of that a particular contamination species in the interior space 11. At this time, the EUV radiation can be switched off. For example, the detector 1 can be a QCM or SAW, which can be used as an online monitor for different species in an EUV lithographic apparatus. Using one or more QCMs and/or SAWs at different temperatures opens the possibility to determine what kinds of gasses are present or leak into the lithographic apparatus, in a simple and relatively inexpensive manner.

For different contaminating species, the threshold pressure values can be different, but can also be relatively close to each other.

Also, a first mono-layer of a certain contamination species can already exist on the monitoring surface 1$a$ due to a different interface process between that species and the monitoring surface 1$a$. This does not change the principle and regions of presently proposed methods and systems, since also in that case, a condensation of the contamination (for example due to a leak) onto the monolayer that is already present can be detected swiftly. In that case, a sudden condensation of a further monolayer can be detected swiftly.

Another aspect of the invention is shown in FIGS. 4-8. In this aspect of the invention, the contamination monitoring system can include: at least one cathode; at least one detector configured to detect electrons that are emitted by said cathode; wherein the cathode can be configured to emit a first current of electrons when the cathode surface is substantially not contaminated by said species, and to emit a second current of electrons when the cathode surface is contaminated by said species.

An embodiment of such a contamination monitoring system 110 is schematically depicted in FIG. 4. The contamination monitoring system 110 of FIG. 4 includes only one cathode 151 having a cathode surface configured to emit electrons into the vacuum 111 during use. For example, the cathode can include at least one relatively sharp tip T for emitting electrons. In FIG. 4, emission of electrons is schematically depicted by an arrow 155. In the FIG. 4 embodiment, a current source 152 is connected to the cathode 151 by wires 157. The current source 152 is configured to generate an electrical current which flows through the cathode 151 during use, heating the cathode 151 to an operating temperature. Alternatively, one or more cold field electron emitters, having one or more electron emitting tips, can be used to emit electrons into the vacuum 111 during use. Such a cold field emitter does not have to be heated to emit electrons during use.

The embodiment 110 of FIG. 4 further includes a detector, which comprises an anode 153 and a current measuring device 154. The anode 153 is configured to receive electrons that are emitted by said cathode 151. For example, the anode 153 can be located in view of the cathode 151. The current measuring device 154 is connected to the anode 153. The current measuring device 154 is configured to measure electron current that is received by the anode 153 during use. The detector can be configured in various other ways. For example, the detector can include an auger detector, which is configured to receive and detect secondary electrons that can be emitted by an anode, when the anode receives primary electrons 155 from the cathode 154. Such an auger detector is schematically depicted at reference sign 158 in FIG. 4, whereas emission of secondary electron is schematically depicted by arrows 156 in FIG. 4. The detector can also be configured in a different way.

Alternatively, a plurality of current detectors, a plurality of cathodes and/or a plurality of anodes can be provided, for example to monitor for contamination at different locations in the apparatus and/or to monitor different contamination species and different concentration levels of a certain contamination species.

During use, in the embodiment of FIG. 4, the cathode 151 is configured to emit—when heated to operating temperature—a first current of electrons when the cathode surface is substantially not contaminated by said contamination species, for example MMA, and to emit a second current of electrons when the cathode surface is contaminated by said contamination species. The second current differs from the first current. For example, good results can be obtained when the cathode surface contains $LaB_6$. It has been found, that the electron emission of a $LaB_6$ containing cathode surface drops significantly under the influence of contamination, for example, contamination which comprises one or more hydrocarbon chains, such as MMA (methylmethacrylate). A $LaB_6$ cathode surface can be arranged in various ways to have the cathode emitting different currents of electrons, depending on whether or not the cathode surface has been contaminated. For example, the cathode surface can contain at least one $LaB_6$ crystal surface, a number of $LaB_6$ crystal grains, and/or $LaB_6$ powder. Alternatively, it is proposed to use or $CeB_6$ instead of $LaB_6$. Also, in an aspect of the invention, the cathode surface is the surface of at least one carbon nanotube. Furthermore, the cathode 151 can be configured to emit electrons substantially as a field emitter, via the cathode tip T. Field emission can occur when the local electrical field at the tip T is enhanced (described by the so called field enhancement factor), for example due to geometrical reasons, i.e., electrons can be emitted by a tunnel process from a relatively sharp cathode tip T towards the anode. For example, the field emitter tip can include the tip of at least one carbon nanotube.

The cathode 151 of the monitoring system can be arranged and formed in various ways. For example, the cathode surface can comprise a flat, curved, 2-dimensional, 3-dimensional surface or a surface of a different shape. The cathode surface can have one or more coatings. For example, the cathode can include a metal wire coated with one or more materials that are suitable to emit said first and second currents of electrons.

The embodiment of FIG. 4 also includes an alarm generator 159 which is connected to the electron detector 154. The alarm generator 159 is configured to generate an alarm signal in case the measure of determined current of electrons, received by said anode, is equal to or less than a certain threshold value.

During use of the embodiment of FIG. 4, the cathode 151 can be heated to an operating temperature by the heating current of the current source 152, such that the cathode 151 can emit a first current of electrons into the vacuum, for the case that a contamination species, to be monitored, is not present in the abutting vacuum environment 111. For example, in case the cathode is a $LaB_6$ containing cathode, the operating temperature can be around 1800° K.+/−about 100° K.

During use of the embodiment of FIG. 4, the current of electrons captured by said anode 153 can be measured for monitoring contamination. The electron current can be detected by one or more detectors, for example, directly by the anode 153 and the current detector 154. The current detector 154 can transmit a detection signal, which signal depends on the current of electrons received by the anode 153, to the alarm generator 159. Analogous, said auger detector 158 can detect the emitted electrons 155 indirectly, via detection of said secondary electrons 156, to generate an electron dependent detection signal which can be transmitted to the alarm generator 159.

When, at a certain time, the contamination species that influences electron emission by the cathode 151, enters the vacuum environment 111, the current of electrons that is emitted by the cathode 151 changes to a second current of electron. For example, in case the cathode surface contains $LaB_6$ and the contamination species contains one or more hydrocarbon chains, the electron emission can drop significantly when the $LaB_6$ cathode surface is contaminated by such species. In the latter case, the electron emission can drop such, that the second current of electrons is about half the first current of electrons, or less. The second electron current can drop to substantially zero. In that case, the above mentioned threshold value can also be substantially zero.

Without wanting to be bound to any theory, it is believed that the high sensitivity to contamination, found in the present invention, can be due to the fact that the cathode acts as a field emitter, wherein contaminants stick to a very tiny fraction of a field emitting tip of the cathode. Field emitters have a very strong electromagnetic field in the vicinity of the tip of the emitter, extracting electrons on the one side, but also accelerating ions (for example contamination molecules) towards the tip in a very focussed way. This focus can be identical to the area from which electrons are emitted. Only a few contamination molecules or only a single large molecule may be enough to negatively influence the field electron emission during use, so that for example the anode current can decrease significantly.

The change in the electron emission results in a change of the current of electrons detected by the electron detector. An alarm signal can be generated in case it is being determined or measured, that the detected current of electrons is equal to or less than the above-mentioned threshold value. The alarm generator 159 can then generate an alarm, for example, to indicate the presence of the contamination in the space 111, to shut down a lithographic process or otherwise. After the contamination has been removed from the vacuum, the cathode 151 can be regenerated and/or cleansed, wherein the contamination is removed therefrom, so that the cathode can be used again in the monitoring of contamination. For example, the heating of the cathode in a clean vacuum environment can result in 'self-cleaning,' i.e., after a while (appr. several seconds to minutes) the cathode can restart emitting electrons. Also, a regenerating compound, for example oxygen, can be supplied to regenerate the cathode. The type of cleansing or regeneration of the cathode can depend on the type of contamination and the type of cathode used.

The use of the contamination monitoring system can be part of a lithographic device manufacturing method.

A contamination monitoring system and method according to the invention can be applied, for example, in Extreme Ultraviolet (EUV) lithographic systems. In that case, the hydrocarbon pressure should be very low in order to prevent carbon growth on the mirrors. By shutting down the EUV source, as soon as contamination has been detected, carbon growth on the mirrors of the lithographic system can be prevented.

Figure 5:
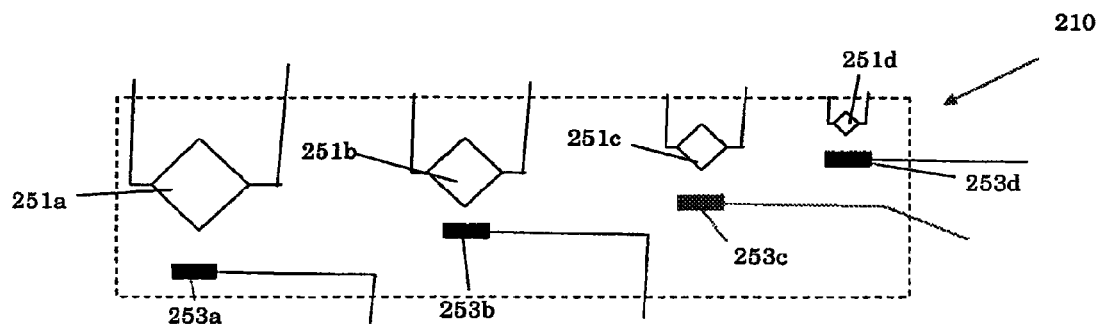
FIG. 5 depicts a third embodiment of a contamination monitoring system.

FIG. 5 depicts part of an embodiment of a contamination monitoring system 210, which differs from the embodiment 110 of FIG. 4 in that the system 210 includes at least two said cathode surfaces having different electron emission surface areas. For example, the embodiment of FIG. 5 includes an array of cathodes 251a, 251b, 251c, 251d, having different surface areas. An array of anodes 253a, 253b, 253c, 253d can be included for receiving electrons from respective cathodes 251a, 251b, 251c, 251d. One or more heaters and current detectors, configured to heat the cathodes 251a-251d and to detect electron currents, respectively, are not shown in FIG. 5. It will be clear to the skilled person, how to arrange and configure the cathodes 251a-251d and anodes 253a-253d, heaters and current detectors, of the embodiment of FIG. 5 to perform contamination monitoring as has been described above with respect to FIG. 4. For instance, an array of contamination monitoring systems can be provided, the system being configured similar to the embodiment of FIG. 4, but having cathodes which differ in electron emission surface area. The different cathodes 251a, 251b, 251c, 251d can provide different sensitivities to contamination, for example at different pressures in the space to be monitored. Also, arrays of field emitters as used in field emission displays can be used.

Figure 6:
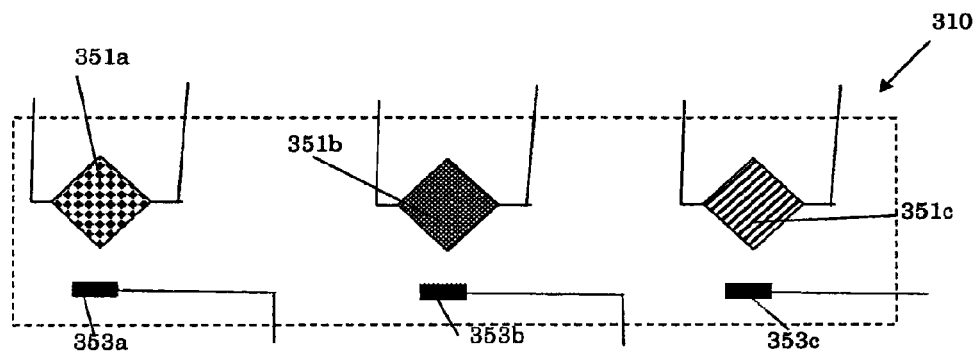
FIG. 6 depicts a fourth embodiment of a contamination monitoring system.
Figure 7:
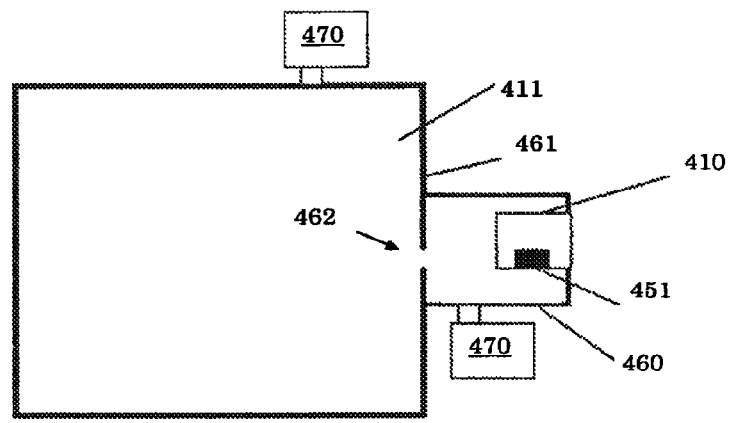
FIG. 7 depicts a fifth embodiment of a contamination monitoring system.

FIG. 6 depicts part of an embodiment of a contamination monitoring system 310, which differs from the embodiment 110 of FIG. 4 in that the system 310 includes at least two said cathode surfaces having different compositions. For example, the embodiment of FIG. 6 includes an array of cathodes 351a, 351b, 351c. The composition of the surfaces of the cathodes 351a-351c can vary in different ways. For instance, the cathode surfaces can differ in materials properties, crystal structure of the cathode surface, crystal grain size at the surface and/or otherwise. As an example, one of the cathode surfaces can contain a powder. Also, in this case, one or more of the cathode surfaces can contain $LaB_6$. One of the cathode surfaces can contains at least one $LaB_6$ crystal surface. Also, said cathode surface can contains a plurality of $LaB_6$ parts, for instance $LaB_6$ crystal grains and/or $LaB_6$ powder. An array of anodes 353a, 353b, 353c is included in the embodiment of FIG. 6 for receiving electrons from respective cathodes 351a, 351b, 351c. Also in this case, one or more heaters and current detectors, configured to heat the cathodes and to detect electron currents, respectively, are not depicted since it will be clear to the skilled person, how to arrange and configure the cathodes 351a-351c and anodes 353a-353c, with heaters and current detectors, to perform contamination monitoring as has been described above.

A cathode of the contamination monitoring system can, for example, be positioned in a main vacuum compartment, having a first vacuum, to be monitored for contamination. Besides, the cathode 451 of the contamination monitoring system 410, and also other parts of the monitoring system 410, can be located in a separate vacuum compartment 460, which compartment 460 is separated from a main compartment 411 to be monitored, as is shown schematically in the embodiment of FIG. 7. The second compartment can have a second vacuum. Then, the second vacuum (or separate compartment 460) can be in fluid communication with the vacuum of the main compartment 411, for example, via an orifice or channel 462 that extends in a separation wall 461. The separate compartment 460 can also be spaced-apart from the main compartment 411, and be linked to the interior of the main compartment via one ore more suitable gas connections.

The separate compartment 460 can be pumped independently from the main vessel 411, creating a differential pumping stage between the two compartments 411, 460. To this aim, one or more pumps 470 can be provided, the pumps 470 being configured for creating a desired differential pumping stage. For example, the dimensions or surface area of the orifice or channel 462 and the pumping speed of the one or more pumps 470 can be chosen in such a way, that during use, the cathode 451 starts emitting said second current of electrons at a predetermined, desired contamination threshold pressure in the main vessel 411. The invention thus can provide a method for monitoring contamination, the method including: locating said at least one cathode in a compartment 460 which is separated from the vacuum 411 to be monitored for contamination; providing a fluid communication between the separate compartment 460 and said vacuum 411; creating a differential pumping stage between the separate compartment and said vacuum.

EXPERIMENT AND RESULTS

As an example, it has been found, that a cathode that contains $LaB_6$ emits less electrons into a vacuum environment thereof in case of the presence of hydrocarbon contamination. For example, the cathode substantially stops emitting electrons when the vacuum environment contains a small amount of MMA contamination.

In an experiment, the embodiment of a contamination monitoring system 110 of FIG. 4 was used. Therein, the cathode 151 used was a $LaB_6$ crystal. An auger detector 158 was used to detect secondary electrons that emanate from the anode 153. Besides the $LaB_6$ cathode, a tungsten cathode was installed, as a reference.

The $LaB_6$ cathode 151 was heated to emit primary electrons into a contamination free vacuum environment. Secondary electrons, resulting from the anode receiving primary electrons, were detected by the auger detector.

After two hours, a small gas flow of MMA contamination was fed into the vacuum environment. The pressure of the flow of MMA contamination was $5 \times 10^{-9}$ torr. In practice, such a small flow of MMA contamination could represent, for example, a small leak or weak outgassing of, for example, resists or insulating materials.

After another four hours, the supply of MMA contamination was halted.

Figure 8:
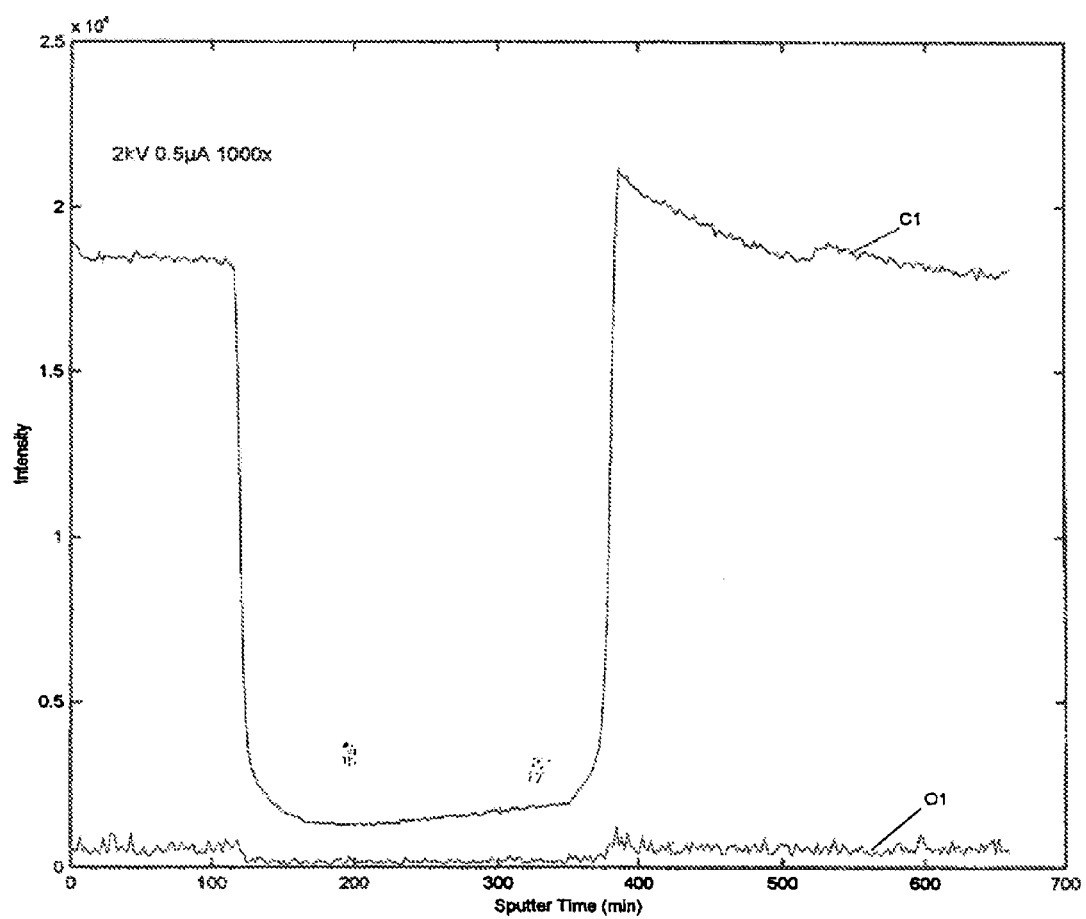
FIG. 8 is a graph showing the influence of a contamination species on electron emission of a $LaB_6$ cathode.

FIG. 8 is a graph showing the result of the example. FIG. 8 shows the carbon auger signal intensities of carbon (C1) and oxygen (O1) as function of the time (minutes). As follows from FIG. 8, in the first two hours, a large number of secondary electrons was detected. Clearly, as soon as the MMA contamination had entered the vacuum, the current of detected secondary electrons dropped significantly. Such a drop was not detected when the tungsten cathode was used instead of the $LaB_6$ cathode. Without wanting to be bound to any theory, the drop of the current of secondary electrons can be contributed to the $LaB_6$ cathode electron emission being suppressed by the MMA contamination. The drop of electron detection was substantially without delay after the MMA had entered the vacuum, leading to a fast response time of the contamination monitoring system. The response time can be a fraction of a second. The response time can be much faster than typical integration times of, for example, a residual gas analyser (RGA).

After supply of MMA had halted, the $LaB_6$ cathode can be regenerated, leading to an increase of primary electron emission. It was found that this increase improved and can be realised more swiftly, when oxygen was supplied to the vacuum environment Also, it has been found that the $LaB_6$ cathode reacts very reproducible to contamination.

A contamination monitoring system according to the present invention can be very sensitive to large hydrocarbon molecules. This system can be based on measuring the current extracted from a cathode, which is very sensitive to contamination of its surface. This system has a fast response to contamination, and can also be used as a 'contamination alarm' sensor, i.e., a contamination threshold security switch in a lithographic projection apparatus.

A $LaB_6$ containing cathode can suddenly stop emitting electrons when about $10^{-9}$ mbar MMA is injected in the vacuum. This means that the contamination monitoring system, including such a cathode, is very sensitive in a critical operating region of an EUV tool.

The contamination monitoring system can also be used to test whether wafers or other substrates, which are to be inserted into a substrate treatment system, lithography apparatus or a different system, are sufficiently clean.

A contamination monitoring system and method can be provided, for example, including a hydrocarbon sensitive cathode material as for instance $LaB_6$. The advantage of this contamination monitoring system/method is its sensitivity, and its simplicity. It can be used for giving a fast contamination alarm.

Although specific reference may be made in this text to the use of lithographic. apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion," respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens," where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g., semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

Besides, various combinations of different embodiments described above and in the Figures and/or the claims can be made. For example, one or more embodiments according to or similar to any of FIGS. 4-7 can be used also in combination with an embodiment according or similar to that of FIG. 2.

What is claimed is:

1. A system for detecting at least one contamination species in a vacuum, the system including:
   at least one cathode having a surface comprising a surface material, the at least one cathode configured to emit electrons into the vacuum; and
   at least one detector configured to detect the electrons emitted by the at least one cathode,
   wherein the cathode is configured to emit a first current of electrons when a cathode surface is substantially not contaminated by the at least one contamination species, and
   wherein the cathode is configured to emit a second current of electrons when the cathode surface is contaminated by the at least one contamination species based on an interaction between the at least one contamination species and the surface material.

2. The system according to claim 1, wherein the surface material comprises Lanthanum Hexaboride.

3. The system according to claim 1, further comprising: at least two cathodes having different surface areas.

4. The system according to claim 1, wherein the at least one detector comprises at least one anode configured to receive the electrons that are emitted by the at least one cathode.

5. The system according to claim 1, further comprising:
an alarm generator configured to generate an alarm signal if the second current of electrons, detected by the at least one detector, is equal to or less than a threshold value.

6. The system according to claim 5, wherein the threshold value is substantially 0.

7. The system according to claim 1, wherein the second current of electrons is approximately equal to, or less than, half the first current of electrons.

8. The system according to claim 1, wherein the at least one contamination species comprises one or more hydrocarbon chains.

9. The system according to claim 1, wherein the surface material comprises at least one carbon nanotube.

10. A lithographic apparatus comprising at least one system according to claim 1.

11. The lithographic apparatus according to claim 10, further comprising:
an illumination system configured to provide a radiation beam;
a patterning device configured to impart the radiation beam with a pattern in its cross-section;
a substrate holder configured to hold a substrate; and
a projection system configured to project the patterned radiation beam onto a target portion of the substrate.

12. The system according to claim 1, wherein the surface material comprises Cesium Hexaboride.

13. A contamination detection system, comprising:
a chamber;
a cathode situated in the chamber, the cathode comprising a surface coated in a surface material being configured to emit electrons as a first current of electrons, the electrons comprising a first current of electrons when the cathode surface is substantially free of contamination from at least one contamination species, and the electrons comprising a second current of electrons when the cathode surface is contaminated by the at least one contamination species based on an interaction between the at least one contamination species and the surface material;
a detector configured to detect the electrons emitted from the cathode; and
a controller configured to generate an alarm signal when the detector detects the second current of electrons.

14. The system of claim 13, further comprising:
a plurality of cathodes situated in the chamber; and
a plurality of detectors corresponding to the plurality of cathodes.

15. The system of claim 14, wherein:
a first cathode from among the plurality of cathodes comprises a first surface coated in a first surface material; and
a second cathode from among the plurality of cathodes comprises a second surface coated in a second surface material.

16. The system of claim 15, wherein the first surface material comprises a different material than the second surface material.

17. The system of claim 13, wherein the surface material comprises Lanthanum Hexaboride.

18. The system of claim 13, wherein the surface material comprises Cesium Hexaboride.

19. The system of claim 13, wherein the second current is less than the first current.

20. The system of claim 13, further comprising:
a current source coupled to the cathode and configured to generate an electric current to heat the cathode to remove the at least one contamination species after the detector has detected the second current of electrons.

* * * * *